United States Patent [19]
Weber

[11] Patent Number: 5,453,086
[45] Date of Patent: Sep. 26, 1995

[54] CARDIAC CATHETER

[76] Inventor: Helmut Weber, Kramerstr. 13, 82061 Neuried, Germany

[21] Appl. No.: 304,771

[22] Filed: Sep. 18, 1994

Related U.S. Application Data

[63] Continuation-in-part of PCT/DE93/00069, Jan. 28, 1993.

[30] Foreign Application Priority Data

Feb. 21, 1992 [DE] Germany .......................... 42 05 336.6

[51] Int. Cl.⁶ ...................................................... A61N 1/05
[52] U.S. Cl. ............................................................. 604/20
[58] Field of Search ..................... 604/20–22; 607/128, 607/120, 115, 116, 119, 122; 606/27, 28, 32, 41

[56] References Cited

FOREIGN PATENT DOCUMENTS 0144764  6/1985  European Pat. Off. .
2639237  5/1990  France .
3718139 12/1988  Germany .

*Primary Examiner*—C. Fred Rosenbaum
*Assistant Examiner*—Manuel Mendez
*Attorney, Agent, or Firm*—Klaus J. Bach

[57] ABSTRACT

In a cardiac catheter comprising a tubular guide catheter having a catheter hose movably disposed therein and electrodes projecting from the hose and forming sensors which are pretensioned so as to extend outwardly when the catheter hose is moved forwardly out of the guide catheter and a fiber disposed in the hose in spaced relationship from the walls of the hose for transmitting light to an area ahead of the catheter, a funnel-shaped foil is connected to the hose and the sensors so as to provide a forwardly open funnel around the axis of the light transmitting fiber when the sensors are extended from the guide catheter for containing rinsing liquid supplied through the annular space between the light transmitting fiber and the hose and for limiting access of blood into the space within the funnel formed by the foil.

5 Claims, 2 Drawing Sheets

CARDIAC CATHETER

This is a continuation-in-part application of International application PCT/DE93/00069 filed Jan. 28, 1993, claiming priority of German application P 42 05 336.6 of Feb. 21, 1992.

BACKGROUND OF THE INVENTION

The invention relates to a cardiac catheter for performing photoablations of heart tissue without risk of damage to the heart.

It is known to provide a cardiac catheter with a probe tip in such a manner that subendocardiac areas can be determined therewith by means of electrodes (Am. J. Cardiol 54: 186–192; 1984). The position of the probe tips however does not remain well determined over an extended period so that a coordination of diagnosis and subsequent therapy is not guaranteed. On the other hand, there are cardiac catheters by which photoablations of heart tissue can be performed by means of laser fibers disposed in the catheter hose (Circulation 71: 579 to 586; 1985). With such heart catheters however, it is possible that the laser fiber comes in direct contact with the endocardium (the heart inner wall membrane) and causes a photodissection of the subendocardium and the myocardium or a perforation of the heart wall.

Further, from DE 37 18 139 C1 a cardiac catheter is known with which the rinsing in the arterial area of the heart is insufficient because of the turbulence in that area.

It is the object of the invention to provide a cardiac catheter of the type referred to above in such a manner that sufficient rinsing with a physiological solution can be achieved in all areas of the heart and which also is of a simplified design.

SUMMARY OF THE INVENTION

In a cardiac catheter comprising a tubular guide catheter having a catheter hose movably disposed therein and electrodes projecting from the hose and forming sensors which are pretensioned so as to extend outwardly when the catheter hose is moved forwardly out of the guide catheter and a fiber disposed in the hose in spaced relationship from the walls of the hose for transmitting light to an area ahead of the catheter, a funnel-shaped foil is connected to the hose and the sensors so as to provide a forwardly open funnel around the axis of the light transmitting fiber when the sensors are extended from the guide catheter for containing rinsing liquid supplied through the annular space between the light transmitting fiber and the hose and for limiting access of blood into the space within the funnel formed by the foil.

The heart catheter according to the invention facilitates the irradiation of selected subendocardiac zones while preventing contact of the quartz fiber tip with the endocardium and displacement of the catheter tip. The formation of a blood clot during laser irradiation is also prevented. This is achieved by the shape of the distal end of the hose which, in accordance with the invention, includes sensors and from which the quartz fiber can be extended in a manner defined with respect to the heart wall inner membrane. As a result, the catheter tip is fixed with respect to the endocardium and, at the same time, the glass fiber tip is held at the required distance from the endocardium. The blood is flushed away by continuous injection of a physiological salt solution through the catheter along the quartz fiber so that during the irradiation a medium is disposed between the fiber tip and the inner heart membrane which is not coagulable.

Because of the funnel-like shaped foil 8 the blood flow is essentially kept away from the irradiation area so that a flush medium flow of about 1 ml/sec is sufficient for an undisturbed irradiation.

With this catheter it has become possible to heal, or example, heart rhythm disturbances, without open heart surgery, without risk of intracardial electroshock, without risk of heart perforation, without thrombosis and embolus formation risks and without full narcosis. Also possibly life-long medication with the known side effects and risks or the installation of electrostimulators such as heart pace makers and cardiovertors/defillibrators can be avoided and, consequently, the quality of life of a patient can be substantially improved and a substantial saving in costs can be achieved. The catheter can also be used in other fields of application such as a thermal or microwave probe.

DESCRIPTION OF A PREFERRED EMBODIMENT

Figure 1:
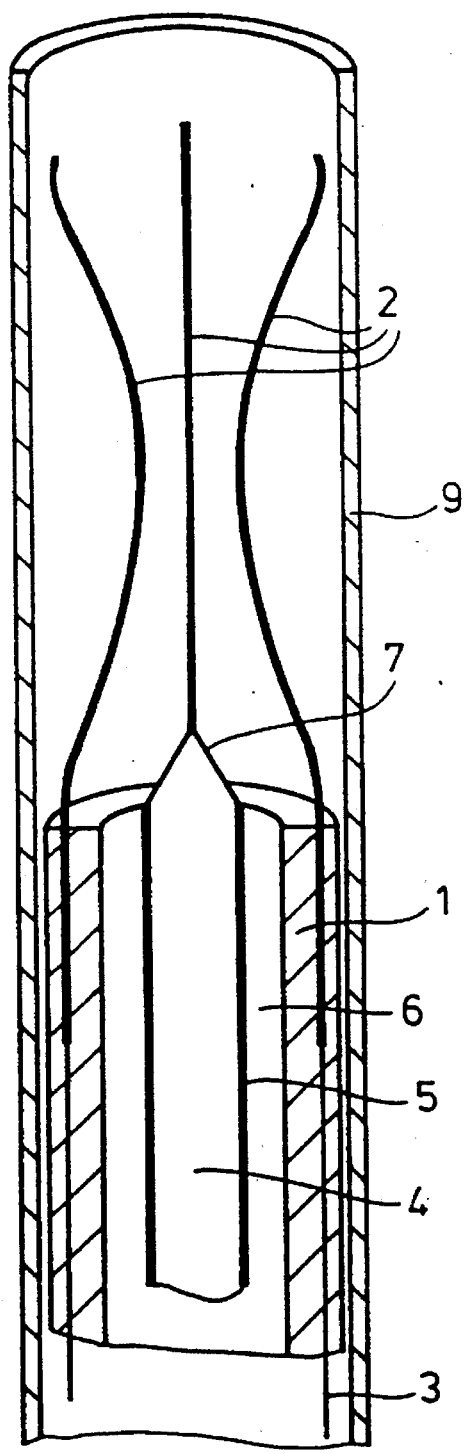
FIG. 1 shows the catheter within a guide catheter 9 (sluice)
Figure 2:
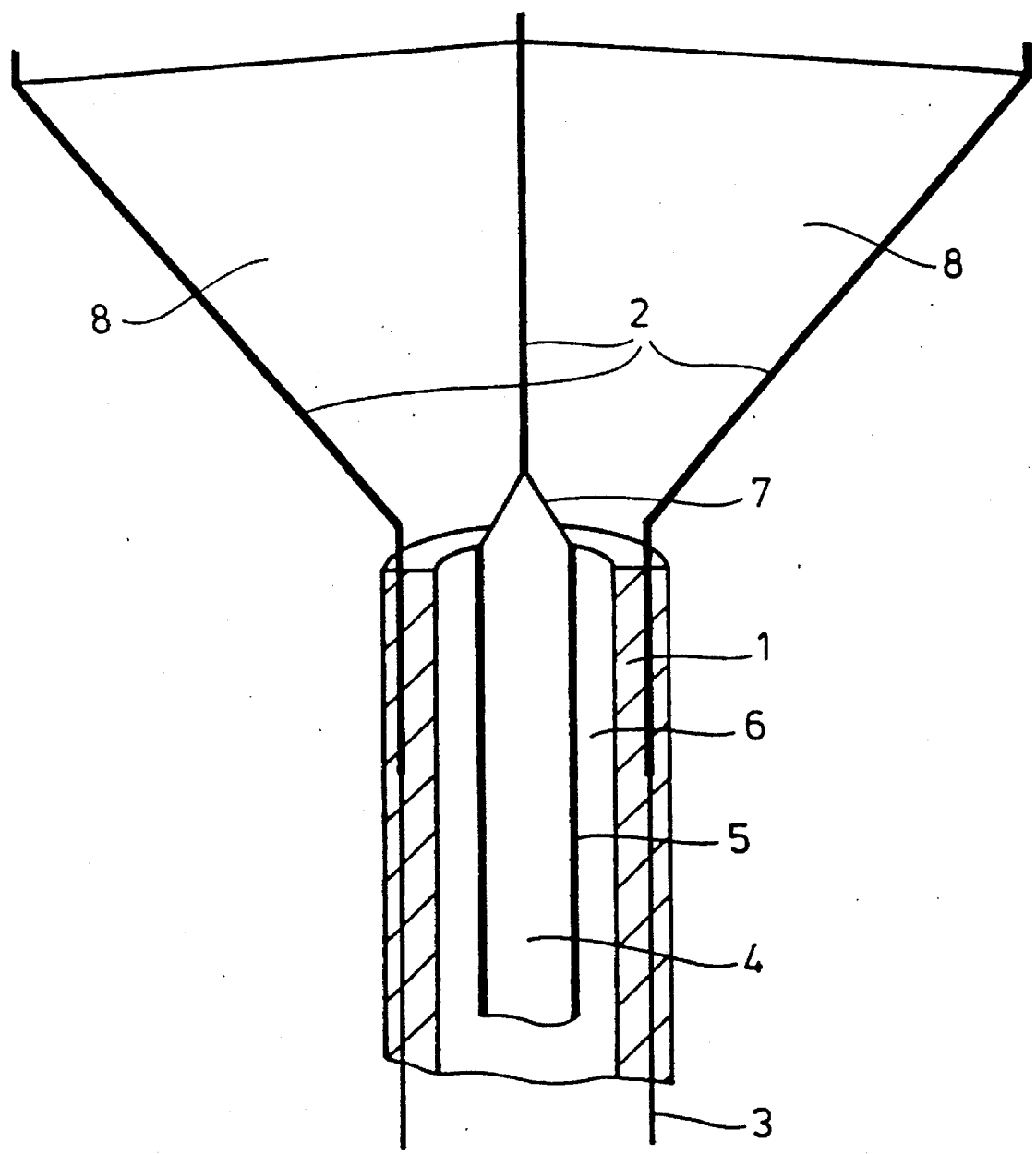
FIG. 2 shows the distal catheter tip with spread electrodes.

FIG. 1 is a cross-sectional view of the distal end of a heart catheter (disposed in a sluice/guide catheter 9). It comprises the end of a hose 1 of plastic material whose front end is formed by an electrode arrangement 2. The electrodes are molded into the distal end of the hose and are firmly fixed therein and electrically separated from one another and they supply their electrical potentials by way of a cable 3 to an analyzing unit which is not shown. Coaxially disposed within the hose 1 is the fiber 4 whose surface is provided with a coating 5. The fiber can be axially guided in the interior 6 of the hose 1. However no guide element is shown. At the distal end of the hose 1 there are provided preferably three electrodes which form sensors 2. They consist of metal wires which are prestressed to have a predetermined shape. The prestressing and length of the sensors 2 are so selected that, at one hand, they center the tip 7 of the fiber 4 and, on the other hand, they can extend outwardly when the distal end of the catheter is moved out of the sluice (guide catheter) 9 toward the heart. A tunnel-shaped foil 8 is mounted to the sensors 2 such that spreading of the sensors causes a toil 8 (membrane) disposed between the sensors to extend (this foil is shown in FIG. 2 but is omitted in FIG. 1 for clarity) whereby the foil stabilizes the distance between the extended sensors and, by surrounding the space between the fiber tip 7 and the endocardiac area to be irradiated, protects that area from strong blood flow. The foil is also connected to the distal end of the hose so that, when extended, it forms a funnel which is open toward the endocardium. As shown in FIG. 2 the sensor tips slightly project forwardly from the funnel-shaped foil 8 for engagement with the endocardium.

FIG. 2 shows the distal catheter tip without the guide catheter 9.

In the position shown, the sensor ends project beyond the tip 7 of the fiber 4 so that the tip 7 does not come into contact with the endocardium. The ends of the sensors are engaged by the endocardium when coming in contact therewith (advancing of the heart catheter) and therefore provide for a fixation/stabilization of the distal intracardiac end of the hose 1 and the fiber 4.

Through the space between the fiber 4, that is, the isolation coating 5 and the inner hose wall, a physiological solution (such as a salt solution) is supplied which exits the end of the hose. In the process it cools the fiber tip and keeps blood out of the space adjacent the end of the hose and the fiber 4 up to the tissue to be irradiated. At the same time the solution prevents blood from entering the catheter system and the formation of blood clots in the irradiation area.

With an outer diameter of the coated fiber 4 of 0.7 mm the inner diameter of the hose should be about 1 mm.

What is claimed is:

1. A cardiac catheter comprising a tubular guide catheter, a catheter hose movably disposed in said guide catheter, electrodes projecting from said hose and forming sensors which are pretensioned so as to normally extend outwardly, said catheter hose having a retracted position within said guide catheter in which said sensors are disposed within and contained by said guide catheter and an extended position in which said sensors axially project from said guide catheter permitting said sensors to extend outwardly, a light transmitting fiber disposed in said hose and having a diameter smaller than said hose such that an annular space remains between said fiber and said hose for supplying rinsing liquid therethrough and a foil connected to said hose and to said sensors, said foil being formed so as to be funnel-shaped in the extended position of said catheter hose in which said sensors are outwardly extended such that said foil forms between said sensors a forwardly open funnel for containing said rinsing liquid in the space ahead of said fiber and limiting access of blood to that space.

2. A cardiac catheter according to claim 1, wherein said sensors are mounted to the distal end of said hose.

3. A cardiac catheter according to claim 1, wherein electric cables for the sensors are disposed in said hose.

4. A cardiac catheter according to claim 1, wherein said fiber is a light conducting fiber.

5. A cardiac catheter according to claim 1, wherein the ends of said sensors project forwardly from the foil attached thereto for engagement with the inner wall of the heart to be contacted thereby.

* * * * *